(12) United States Patent
Zolli

(10) Patent No.: US 8,398,578 B1
(45) Date of Patent: Mar. 19, 2013

(54) CAPSULE FRIENDLY TIPS FOR PHACOEMULSIFICATION AND FOR IRRIGATION/ASPIRATION

(76) Inventor: Christine Lydie Zolli, Oldwick, NJ (US)

( * ) Notice: Subject to any disclaimer, the term of this patent is extended or adjusted under 35 U.S.C. 154(b) by 389 days.

(21) Appl. No.: 12/794,715

(22) Filed: Jun. 4, 2010

Related U.S. Application Data

(60) Provisional application No. 61/184,399, filed on Jun. 5, 2009.

(51) Int. Cl.
*A61N 1/30* (2006.01)
(52) U.S. Cl. .................. 604/19; 604/275; 606/107
(58) Field of Classification Search ............ 604/19, 604/27, 35, 40, 158, 198, 273, 264, 272, 604/275; 606/39, 161, 107
See application file for complete search history.

(56) References Cited

U.S. PATENT DOCUMENTS

| | | | | |
|---|---|---|---|---|
| 4,657,772 A | * | 4/1987 | Kocak | 427/2.28 |
| 6,126,629 A | * | 10/2000 | Perkins | 604/22 |

* cited by examiner

*Primary Examiner* — Theodore Stigell
(74) *Attorney, Agent, or Firm* — Hess Patent Law Firm LLC; Robert J. Hess

(57) ABSTRACT

A surgical tool whose shaft terminates into a tip having a smooth, rounded edge and that has pores on its top or side, but none one the underside of its base. There may be a flattened base indicative of the shape of a bubble, basket, funnel, circular disc, oblong shape, Maltese cross or mulberry. The pores may be directed backward. A spring spiral may be provided within the shaft to exert a spring bias. The globe may be in the form of a sleeve fitted over a conventional phacoemulsification tip and needs to be positioned to keep the phacoemulsification tip from contacting the sleeve during operation. Alternatively, the globe may be part of a tip itself.

12 Claims, 11 Drawing Sheets

US 8,398,578 B1

CAPSULE FRIENDLY TIPS FOR PHACOEMULSIFICATION AND FOR IRRIGATION/ASPIRATION

CROSS-REFERENCE TO COPENDING PATENT APPLICATIONS

The present application claims the benefit of priority from provisional patent application Ser. No. 61/184,399 filed Jun. 5, 2009.

BACKGROUND OF THE INVENTION

One aspect of the invention relates to surgical tools in the form of an elongated shaft and tip suited for use in phacoemulsification surgical instruments and irrigation-aspiration instruments.

Conventional phacoemulsification tips are sharp and have an overly large port that admits the eye capsule in a blink-of-an-eye. The eye capsule, when sucked into the overly large port, puckers and rips to produce rapidly widening tear lines through which vitreous prolapses, which often leads to vitreous loss. Therefore, the use such conventional phacoemulsification tips that are sharp with the overly large port run the risk of causing capsule ruptures, which is a very serious intraoperaive, i.e., surgical, complication.

There is therefore a need to reduce such a risk of causing capsule ruptures, i.e., by avoiding the use of conventional phacoemulsification tips that are sharp and that have an overly large port. That is, there is a need for phacoemulsification tips that are safe in the sense that they are not as likely to cause capsule ruptures. That is, the surgical tool should be "capsule friendly" to lessen the likelihood of creating capsule ruptures during their use in phacoemulsification surgical procedures or in irrigation-aspiration applications of the eye.

SUMMARY OF THE INVENTION

One aspect of the invention resides in "capsule friendly" tips suited for use with Alcon, Inc.'s INFINI and LEGACY units, as well as for all other phacoemulsification type machines, that achieve safe removal of cataract fractions without sucking in iris tissue or pulling in and thus rupturing the capsule. The "capsule friendly" tips are constructed so only the aspiration of soft cortex occurs. That is, the capsule cannot enter the smooth rounded "bubble" type tips with pores too small to admit the capsule under suction. Further, the smooth, rounded surfaces of the tips form no regions of sharpness that might otherwise cut into the capsule during aspiration. For instance, there are intersecting planar surfaces in such smooth, rounded surfaces of the tips.

In accordance with the invention, the tips are configured as (a) rounded, smoothly polished globe-like tips ("bubble" or "basket" tips), with multiple small pores (such as 0.3 mm or lower) on the surface and (b) as shaft tips with the aspiration prevented by wire guards from sucking in the capsule and iris. The pores admit only emulsified proteinaceous material, which leaves the capsule and the iris alone. In use, the tips are located at a distal end of a phacoemulfication ultrasonic surgical hand piece and/or an irrigation/aspiration surgical hand piece.

BRIEF DESCRIPTION OF THE DRAWING

For a better understanding of the present invention, reference is made to the following description and accompanying drawings, while the scope of the invention is set forth in the appended claims.

DETAILED DESCRIPTION OF THE INVENTION

Figure 1:
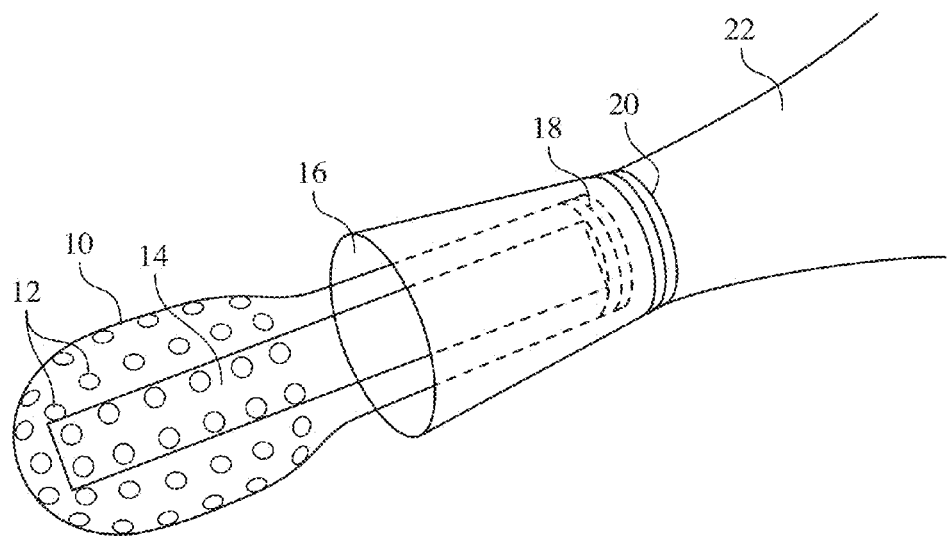
FIG. 1 is an isometric view of a basket sleeve tip embodiment in accordance with the invention in which a basket sleeve with pores is placed onto a conventional distal tip of an ultrasonic phacoemuslfication surgical hand piece.
Figure 2:
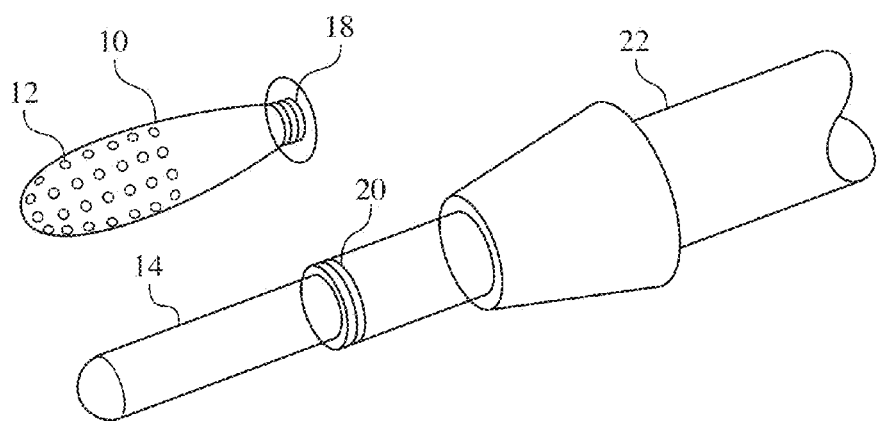
FIG. 2 is an exploded, isometric view of the basket sleeve tip embodiment in accordance with FIG. 1 prior to inserting a conventional distal tip of an ultrasonic phacoemuslfication surgical hand piece into a basket sleeve with pores and prior to mating internal grooves of the basket sleeve with external grooves on the outside of the hand piece.
Figure 3:
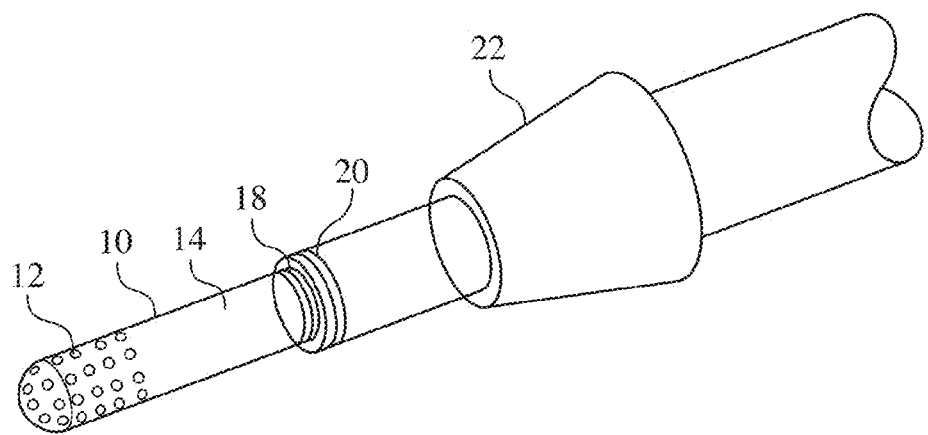
FIG. 3 is an isometric view of the basket sleeve tip secured to the ultrasonic phacoemuslfication surgical hand piece in accordance with the embodiment of FIGS. 1 and 2.
Figure 4:
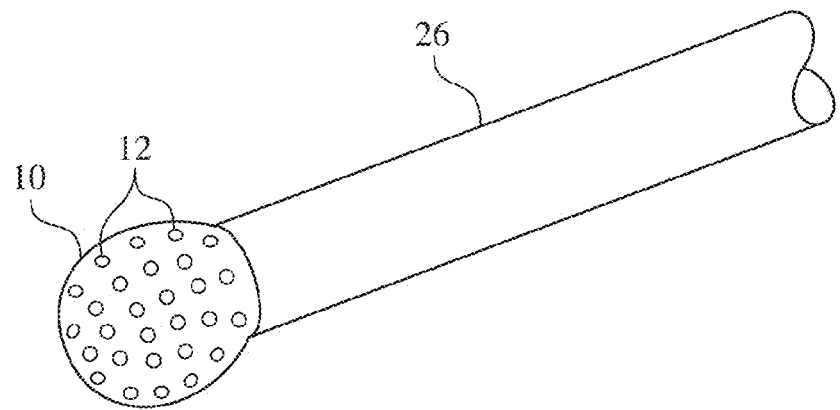
FIG. 4 is isometric end view of the basket sleeve tip of FIGS. 1-3.
Figure 5:
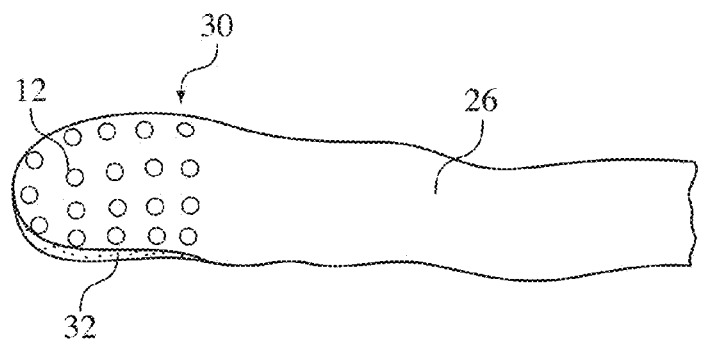
FIG. 5 is isometric view of a one-piece basket tip embodiment in accordance with the invention in which a basket tip with pores is integrally formed in a one-piece construction with a shaft or needle of an ultrasonic phacoemuslfication surgical hand piece to constitute a distal tip of the hand piece.
Figure 6:
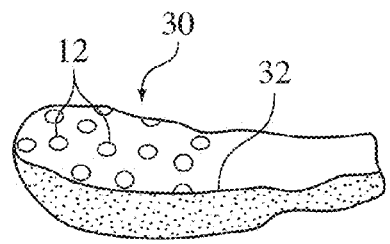
FIG. 6 is an enlarged isometric view of the one-piece basket tip embodiment of FIGS. 4-5, but showing more of the base than in FIG. 5.
Figure 7:
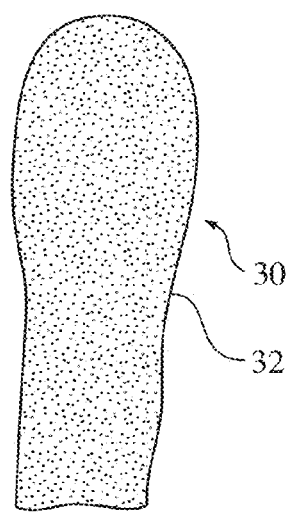
FIG. 7 is a bottom view to show the base of the one-piece basket tip embodiment of FIGS. 5-6.
Figure 8:
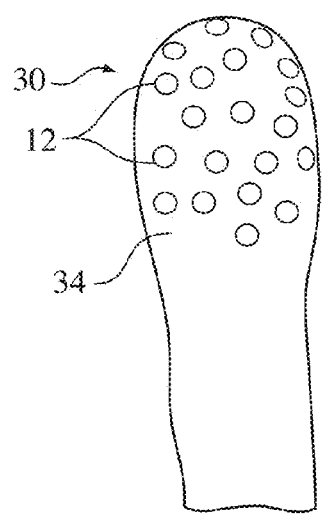
FIG. 8 is a top view to show the top of the one-piece basket tip embodiment of FIGS. 5-6.

All tips in accordance with the FIGS. 1-8, 11-22 of the invention have a rounded, almost spherical, upper two-thirds (⅔) of their shape and are dotted with pores, whose number depends upon what is practical with conventional pore making techniques (i.e., 3 holes, 5 holes, n holes). The tips of FIGS. 1-8, 11-14 have a somewhat flatter solid base so there is no aspiration from below, but rather only from around the sides and from the top. The tip design aims to provide a smooth, rounded outer surface without sharp edges and with openings (pores) small enough so as to not suck in the eye capsule.

FIGS. 1-9, 11-14 show tips are configured as rounded, smoothly polished globe-like tips ("bubble" tips 30 or "basket" tips 10), with multiple small pores 12 (such as 0.3 mm or less) on the surface. Indeed, a pore size smaller than 0.3 mm will suffice. The pores 12 admit only emulsified proteinaceous material, which leaves the capsule and the iris alone. In use, the tips 10, 30 are located at a distal end of a phacoemulsification ultrasonic surgical hand piece 22 (which may have an infusion sleeve 16) and/or an irrigation/aspiration surgical hand piece.

The tips of FIGS. 1-20 include surgical hand piece tips that are suited for ultrasonic phacoemulsification (U-Phaco) type applications, irrigation/aspiration (I/A) type applications or both types of applications. The U-phaco type tips include a) a basket sleeve 10 added onto a conventional phacoemulsification surgical hand piece tip 14 and b) a basket tip one-piece construction 30 that is integrally formed with the conventional phacoemulsification surgical hand piece. The I/A type tips include c) a straight bubble tip 40, d) a curved bubble tip 50, e) a kugeln type tip 60 and f) a spring assisted tip 70. The tips for both applications (U-Phaco and I/A) include g) cross-bun or Maltese cross guard tips 80. All embodiments of tips in accordance with the invention may be designed with a spring-loaded feature that employs a spring spiral in the tip shaft as discussed in connection with the discussion that follows regarding the f) spring assisted tip.

Basket Sleeve 10 on an Existing Tip 14 (FIGS. 1-4)

The conventional phacoemulsification tip 14 has outside grooves 20 to which could be fastened a basket sleeve 10 configured with mating internal grooves 18 in accordance with this embodiment of the invention. Thus, the basket sleeve 10 may be screw threaded via its internal grooves 18 onto the exterior grooves 20 of the tip 14.

Preferably, the basket sleeve 10 is made of a transparent material such as methylmethacrylate and sufficiently rigid to maintain its shape without collapsing onto the conventional phacoemulsification tip 14 while exposed to fluid pressures from ultrasonic speed operation. Further, the basket sleeve 10 is sized to allow the conventional phacoemulsification tip 14 to oscillate to and fro freely, but clear of the walls of the basket sleeve 10 so that the conventional phacoemulsification tip 14 in its longest excursion to-and-fro would never touch the wall of the basket sleeve 10. Such oscillating motion is of benefit in disrupting cataract tissue over tiny distances such as up to 1 mm away from the oscillating tip. This result is based on clinical observations that ultrasound energy breaks tissue from a distance.

Basket Tip 30 in One-Piece Construction (FIGS. 5-9, 10-11)

The material of the basket tip 30 may be stainless steel or other materials used in forming conventional phacoemulsification tips. The basket tip 30 has a hollow, elongated shaft 26 that terminates at, and is in fluid communication with, a hollow globe having a base 32 and a top 34. The base 32 rises to about ⅓ of the total height of the basket tip 30 and the top 34 rises to about ⅔ of the total height of the basket tip 30 in the horizontal orientation of FIG. 6. The top 34 is smooth, rounded with pores 12. The base 32 has no pores and may be flat with a straight base. The pore diameter of the pores 12 may be ¼ mm or ½ mm and arranged along a pin shaft 36 of FIG. 9.

Figure 10:
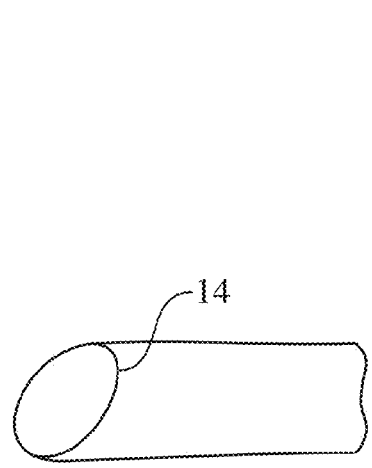
FIG. 10 is a conventional sharp edge phacoemulsification tip.
Figure 9:
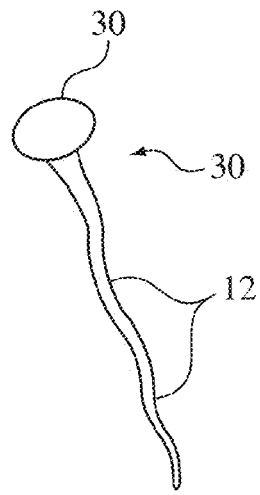
FIG. 9 is a pin shape in accordance with a further embodiment of the invention.

Turning to the conventional phacoemulsification tip 14 of FIG. 10, the sharp edges and open center of the conventional phacoemulsification tip 14 contrasts markedly to the smooth, round top 34 of the tip 30. Such sharp edges create the risk of snagging into tissue during passage through an incision to damage the same, which risk of snagging to cause tissue damage is considerably lessened with the smooth rounded tips of the present invention.

Figure 11:
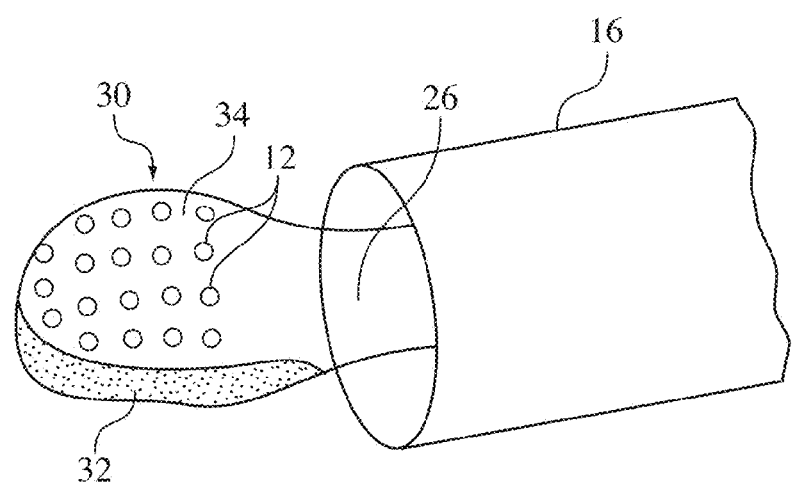
FIG. 11 is an isometric view of a bubble tip embodiment in accordance with the invention shown protruding from a sleeve.
Figure 12:
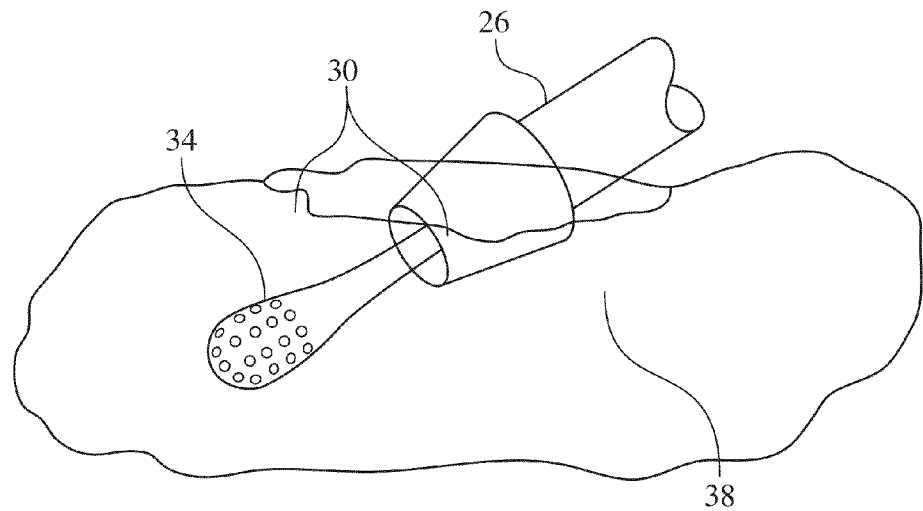
FIG. 12 is an isometric view of the bubble tip embodiment of FIG. 11 inserted into an eye capsule.

FIG. 11 shows the globe of the basket tip 50 projecting beyond an end of an infusion sleeve 16. The globe of the basket tip 50 includes a top 34 and the base 32 of the basket tip 50 at a distal end of the shaft 26. Only the top 34 has pores 12. FIG. 12 illustrates the insertion of the globe of the basket tip 30 through an incision to enter confines of the eye capsule 38, with the elongated, hollow shaft 26 extending to the outside of the capsule.

Straight Bubble Tip 40

Figure 13:
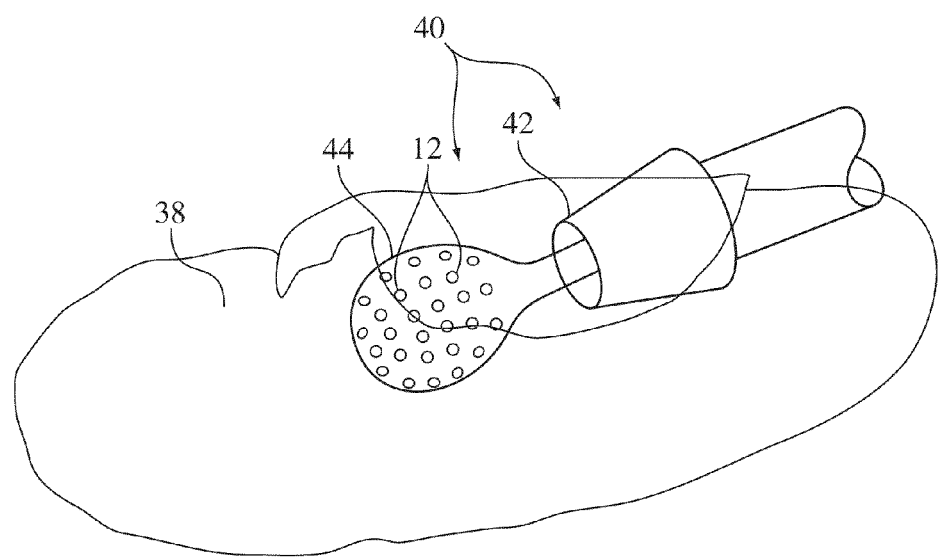
FIG. 13 is an isometric view of a curved bubble tip embodiment in accordance with the invention in which an irrigation/aspiration shaft or needle curves to terminate into a globular shape with pores to constitute a distal tip of an irrigation/aspiration surgical hand piece.

Turning to FIG. 13, the straight bubble tip 40 is shown inserted through an incision into the eye capsule 38. The bubble tip 40 includes an elongated, hollow shaft 42 that extends in a substantially straight manner to a hollow globe 44 that has multiple pores 12 on its surface.

Curved Bubble Tip 50

Figure 14:
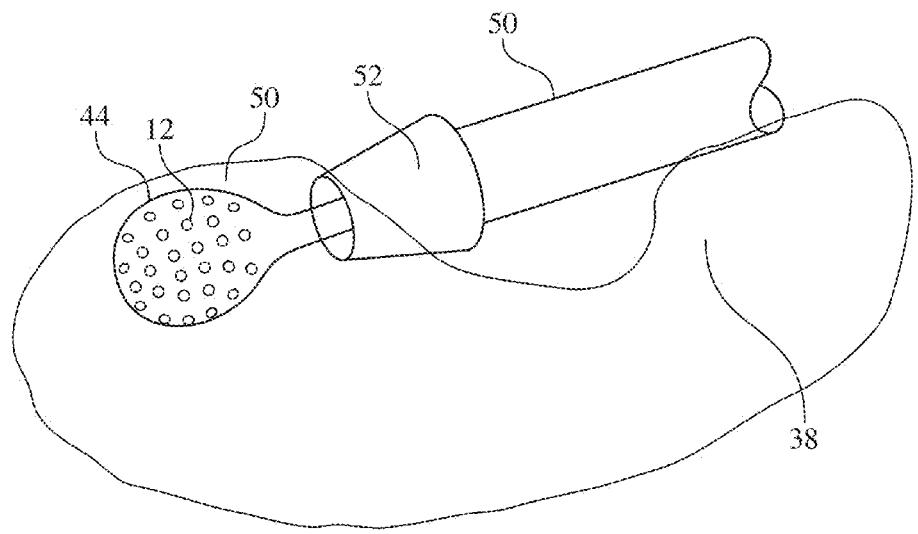
FIG. 14 is an isometric view of a straight bubble tip embodiment in accordance with the invention in which a straight irrigation/aspiration shaft or needle terminates into a globular shape with pores to constitute a distal tip of an irrigation/aspiration surgical hand piece.

Turning to FIG. 14, the curved bubble tip 50 is shown inserted through an incision into the eye capsule 38. The curved bubble tip 50 is elongated so that its hollow, elongated shaft 52 extends in a curved manner to terminate into a hollow globe 44 with multiple pores 12 on its surface. The curvature enables positioning of the globe 44 into regions that may not otherwise be as accessible if a straight bubble tip 40 were used instead.

Kugeln Tip 60, 62, 64

Figure 15:
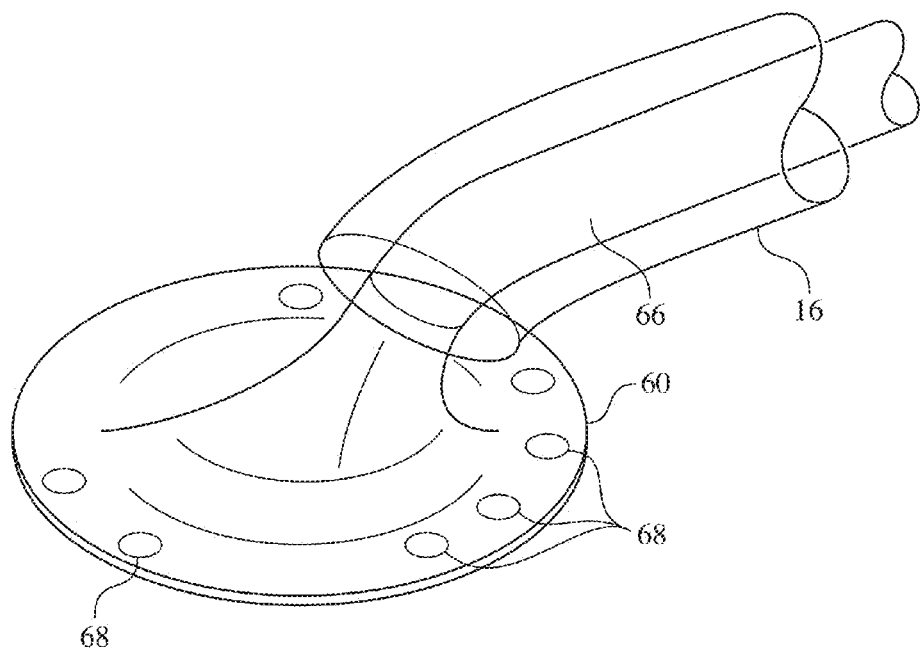
FIG. 15 is an isometric view of a funnel style kugeln tip embodiment in accordance with the invention in which an irrigation/aspiration shaft or needle curves to terminate into a funnel shape with pores directed backward to constitute a distal tip of an irrigation/aspiration surgical hand piece.
Figure 16:
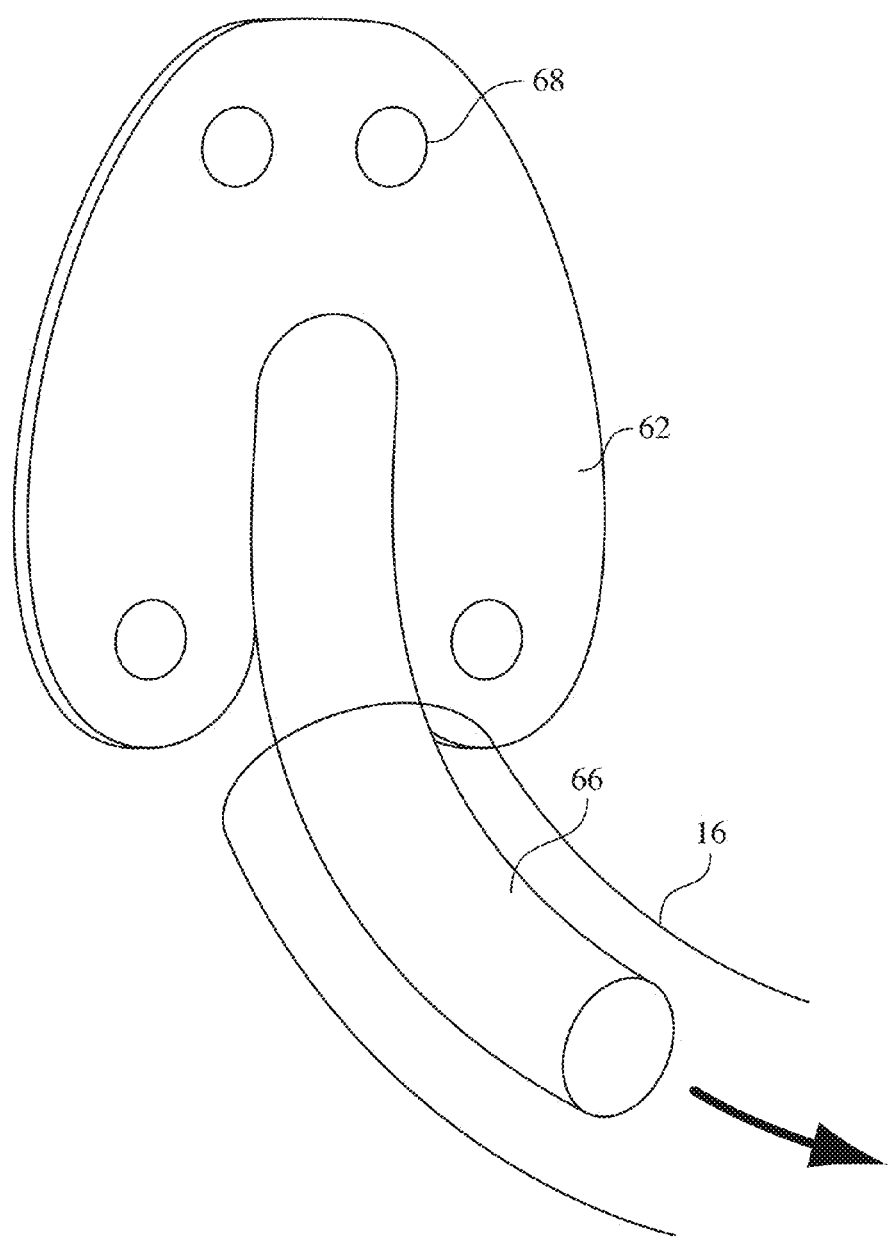
FIG. 16 is an isometric view of a horseshoe style kugeln tip embodiment in accordance with the invention in which an irrigation/aspiration shaft or needle curves to terminate into a horseshoe shape with pores directed backward to constitute a distal tip of an irrigation/aspiration surgical hand piece.
Figure 17:
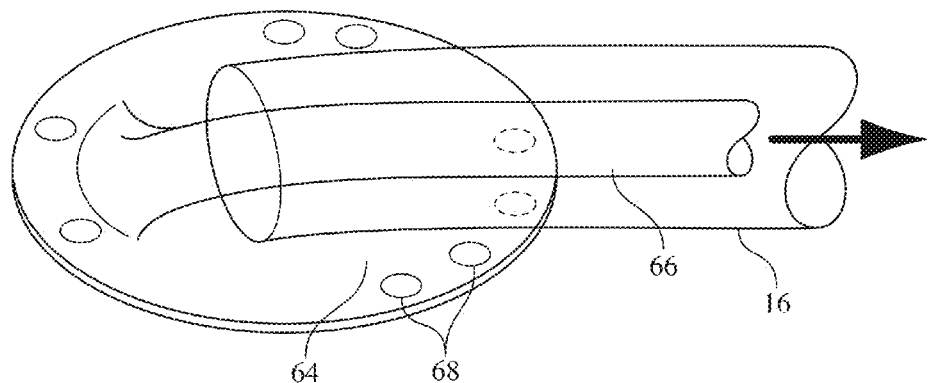
FIG. 17 is an isometric view of an oblong "Retro" style kugeln tip embodiment in accordance with the invention with longer backward reach in which an irrigation/aspiration shaft or needle curves to terminate into a oblong shape with pores directed backward to constitute a distal tip of an irrigation/aspiration surgical hand piece.

Turning to FIGS. 15-17, kugeln tips in accordance with different embodiments of the invention are shown each with a face with pores directed backward toward the surgeon to facilitate the removal of hard-to-get cortex under the port of entry, which is usually the 12 o'clock cortex.

In the case of FIG. 15, a funnel type kugeln tip is shown having a circular disc shaped globe 60 and an irrigation/aspiration shaft or needle 66 that extends within an infusion sleeve 16. The shaft or needle 66 terminates into a funnel shape that diverges at a transition into a face of the circular disc shaped globe 60. The pores 68 are directed backward and arranged in the face of the circular disc shaped globe 60 on the same side of the circular disc shaped globe 60 where the shaft or needle 66 funnels into the circular disc shaped globe 60.

In the case of FIG. 16, a horseshoe style kugeln tip is shown with a horseshoe shaped globe 62 and an irrigation/aspiration shaft or needle 66 that extends within an infusion sleeve 16.

The shaft or needle 66 terminates into the horseshoe shaped globe 62. The pores 68 are directed backward in the horseshoe shaped globe 62 on the same side of the globe 62 from which approaches the shaft or needle 66 to reach the horseshoe shaped globe 62.

In the case of FIG. 17, an oblong "Retro" style kugeln is shown having an oblong globe 64 with a longer backward reach that in the case of the embodiments of FIGS. 15 and 16. The irrigation/aspiration shaft or needle 66 of FIG. 17 extends within an infusion sleeve 16 and terminates into the oblong globe 64. The oblong globe 64 has pores 68 that are directed backward on the same side of the oblong globe 64 that the shaft or needle 66 reaches the oblong globe 64.

Spring Assisted Tip 70

Figure 18:
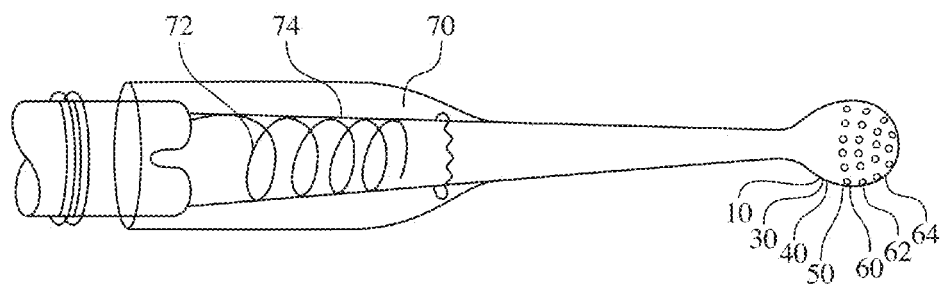
FIG. 18 is an isometric view of a spring assisted tip embodiment in accordance with the invention that includes a spring spiral within a shaft of a surgical hand piece.

Turning to FIG. 18, the spring assisted tip 70 or spring loaded tip has a delicate spring spiral 72 within its shaft 74 that allows the surgeon (user) to press the tip gently against the cortex against the spring bias. The spring spiral 72 then recoils under bias (since it has as tendency to do so) and effectuates minimal movement against the cortex and allows onion like layers to loosen their compactness and be aspirated into the pores faster than without the spring action. The distal end of the spring-assisted tip 70 may be adopted for any of the tip embodiments of the present invention.

Cross-Bun or Maltese Cross Guard Tips 80 for Both U-Phaco and I/A Hand Pieces

Figure 19:
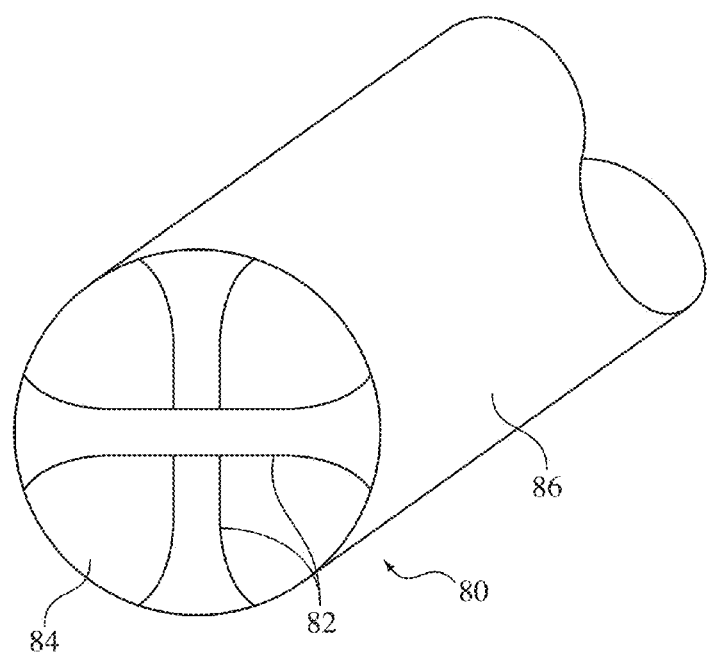
FIG. 19 is an isometric end view of a cross-bun or Maltese cross tip embodiment in accordance with the invention.
Figure 20:
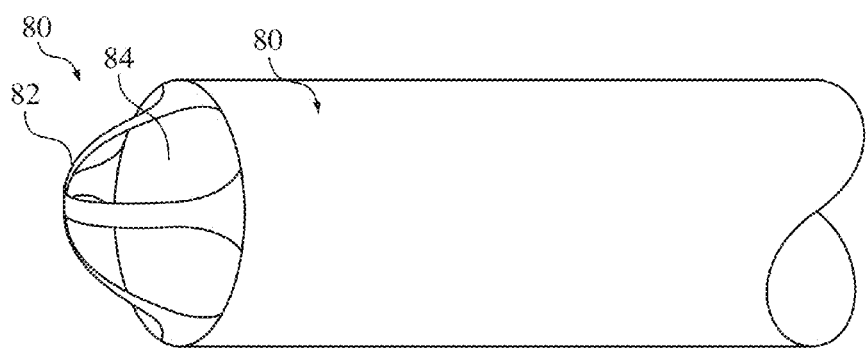
FIG. 20 is an isometric side view of a cross-bun or Maltese cross tip embodiment in accordance with FIG. 19.

Turning to FIGS. 19-20, the cross-bun or Maltese cross guard tips 80 resemble conventional U-Phaco and I/A tips the most out of all the embodiments and thus are likely the easiest to retool an existing tip manufacturing facility and thus the easiest for a conventional tip manufacturer to produce. Both U-Phaco and I/A type cross-bun or Maltese cross guard tips 80 look somewhat alike in that the aspiration port of each is located dead front and each has a built-in guard that is all one-piece with the tip.

The globe of the tip of the cross-bun or Maltese cross type is constituted by two wire arms 82 made of fine smooth micro wires that straddle crosswise the port 84 of an elongated, hollow shaft 86. They minimally bulge to appear slightly rounded and not sharp and connect to the edges of the port widened a bit, as if in shape of a Maltese cross. The two wire arms 82 cross at 90 degrees across the port 84, thereby dividing the port 84 into four smaller entrances that are each too small for the capsule to enter. The emulsified matter, however, flow faster through the wires, but then quickly join together to flow the full sized channel downstream of the wire part of he port to continue to be aspirated in accordance with the flow dynamics of conventional tips.

Figure 21:
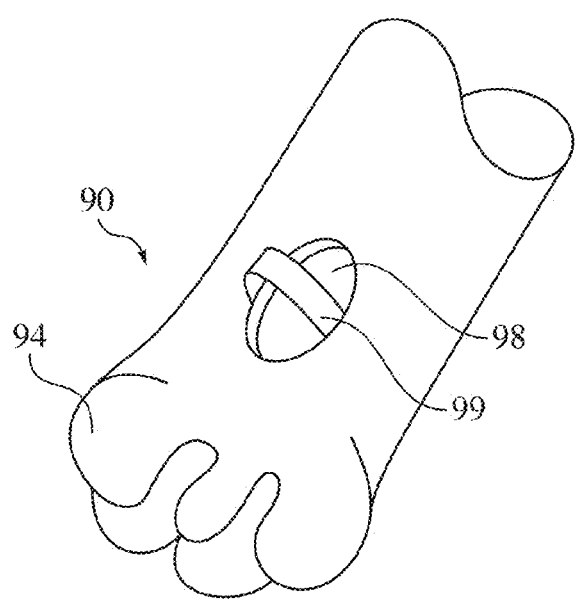
FIG. 21 is an isometric view of a mulberry tip in accordance with a straight shaft embodiment of the present invention.
Figure 22:
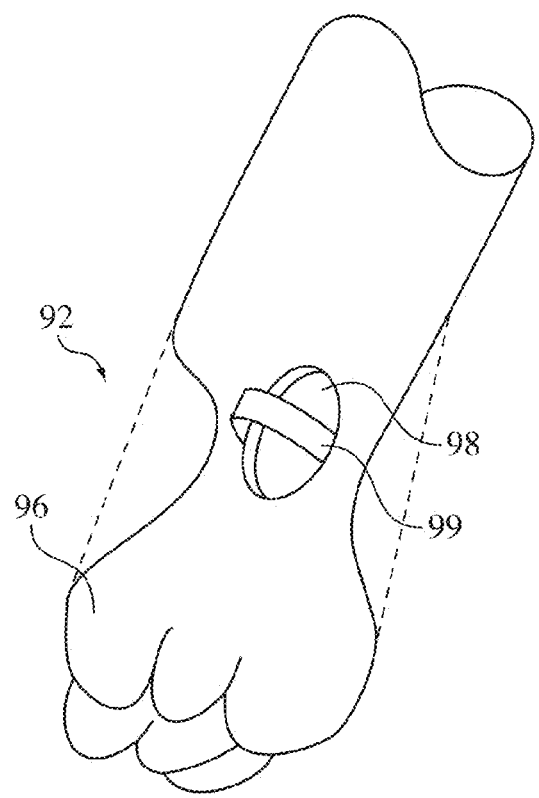
FIG. 22 is an isometric view of a mulberry tip in accordance with an indented shaft embodiment of the present invention.

Turning to FIGS. 21 and 22, two types of mulberry tips 90, 92 are shown, i.e., FIG. 21 is for a straight phaceoemuslfication shaft and FIG. 22 is for an indented phacoemulsification shaft. The size of the shaft for each type of mulberry tip 90, 92 is the same as that of a shaft of a conventional phacoemulsification tip 100 of FIG. 23. The conventional phacoemulsification tip 100 in this example has an end that is to smooth and thus just compresses the cortex material to shrivel it up so it could be aspirated better.

Figure 23:
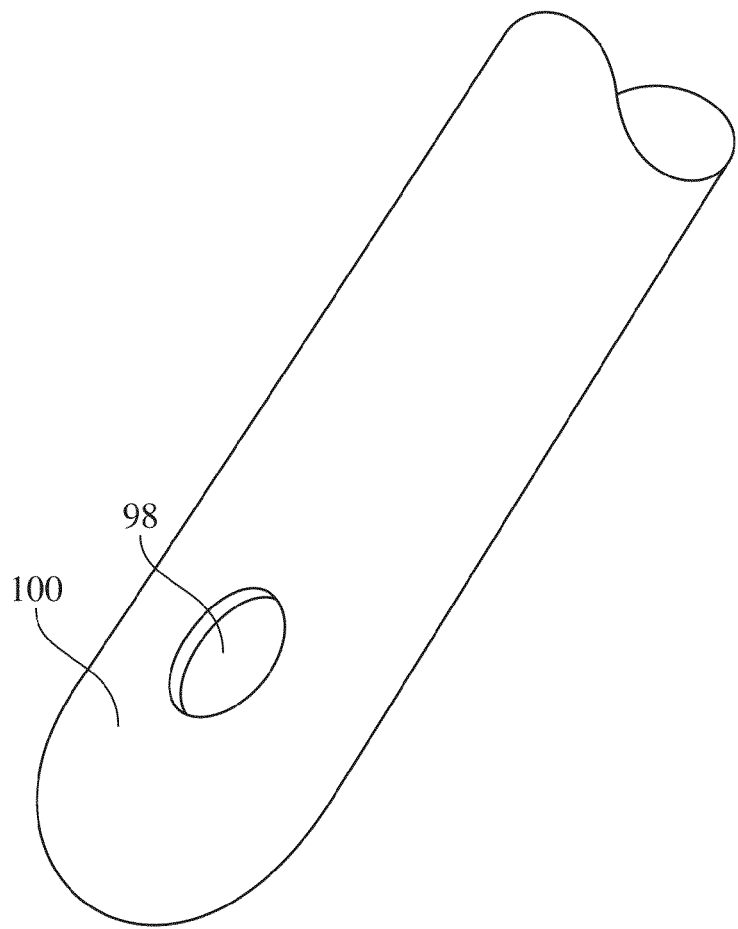
FIG. 23 is an isometric view of a conventional phacoemulsification tip.

Each mulberry tip 90, 92 has a respective irregularity shape 94, 96 that is configured to engage epinucleus cortical material to work as a "battering ram" to divide cortical fibers so they can become dislodged and be aspirated with more ease than for conventional phacoemulsification tips 100 of FIG. 23. For instance, the irregularity shape 94, 96 may take the form of a plurality of rounded protrusions that extend in a direction of elongation of the shaft (from which the mulberry tip extends). The rounded protrusions may be arranged concentric with a center axis of the tip and may be arranged in a symmetrical manner.

Further, the hole, port or opening 98 for aspiration has a wire 99 across it if the hole, port or opening 98 for aspiration is otherwise the same dimension as is found in conventional phacoemulsification tips 100 of FIG. 23 to compensate for the overly large dimension of the hole, port or opening 98. That is, "overly" in the sense of being capable of admitting the capsule during aspiration due to the overly large dimension of the hole, port or opening 98.

In the case of the "capsule friendly" tips as depicted in all the embodiments of the present invention, such may be used as the irrigation-aspiration tips for all models and makes of conventional irrigation-aspiration handpieces utilizing in phacoemulsification consoles by conventional manufacturers. The choice of material for the "capsule friendly" tips of any of the embodiments of the present invention may include that of metal or hardened silicone.

While the foregoing description and drawings represent the preferred embodiments of the present invention, it will be understood that various changes and modifications may be made without departing from the scope of the present invention.

What is claimed is:

1. A capsule friendly surgical tool, comprising an elongated shaft extending between a proximal end and a distal end and being hollow through a length of the elongated shaft, the distal end terminating into a tip having a curved portion with a porous region and having a base portion free of any pores, the curved portion covers a top of the tip and top of sides of the tip, the base portion covers a bottom of the tip and a bottom of sides of the tip, each of the curved portion and the base portion having a respective height, the respective heights of the curved portion and the base portion together defining a diameter of the tip and being transverse to the length of the elongated shaft, the respective height of the curved portion being greater in dimension than the respective height of the base portion, the tip being smooth and rounded so as to be free of sharp edges, the base portion being flatter than the curved portion, the porous region having pores in fluid communication with the hollow of the elongated shaft, each of the pores of the porous region having a diameter of at most 0.3 millimeters.

2. The capsule friendly surgical tool of claim 1, wherein the height of the curved portion is substantially twice the height of the base portion.

3. The capsule friendly surgical tool of claim 1, wherein the proximal end of the elongated shaft has interior grooves; further comprising a surgical hand piece having exterior grooves configured and arranged to mate with the interior grooves of the elongated shaft to retain the elongated shaft and the surgical hand piece together as the interior grooves of the shaft complete being fitted onto the exterior grooves of the surgical hand piece.

4. The capsule friendly surgical tool of claim 3, wherein the elongated shaft constitutes a sleeve, the surgical hand piece including a hollow body that terminates at an open distal end, the open distal end being inserted into confines of the sleeve to be positioned neighboring the pores of the porous region, the sleeve being made of a sufficiently rigid material to prevent collapsing onto the hollow body that would otherwise create a risk contact with the hollow body.

5. The capsule friendly surgical tool of claim 1, further comprising a surgical hand piece that includes a hollow body that terminates at an open distal end, the open distal end and an interior wall of the elongated shaft being spaced from each other with the open distal end neighboring the pores of the porous region.

6. The capsule friendly surgical tool of claim 1, further comprising a coiled spring spiral within the shaft that compresses under manual pressure in a direction against bias so that as the manual pressure is removed the coiled spring spiral has a tendency to recoil in an opposite direction under bias.

7. The capsule friendly surgical tool of claim 1, wherein the elongated shaft extends in a substantially straight manner.

8. The capsule friendly surgical tool of claim 1, wherein the elongated shaft has curvature so as to extend in a substantially curved manner.

9. The capsule friendly surgical tool of claim 1, further comprising an infusion sleeve, the elongated shaft being inserted into the infusion sleeve, the tip being clear of the infusion sleeve.

10. The capsule friendly surgical tool of claim 1, further comprising a surgical hand piece from which extends the shaft, the surgical hand piece being configured to be operative to carry out phacoemulsification at ultrasonic speeds.

11. The capsule friendly surgical tool of claim 1, further comprising an aspiration/irrigation sleeve, the shaft extending within the sleeve in a manner that defines a gap between an inner wall of the sleeve and an outer wall of the elongated shaft to enable fluid flow through the gap.

12. The capsule friendly surgical tool of claim 1, wherein each of the pores only has a diameter smaller than 0.3 millimeters.

* * * * *